United States Patent [19]

van Wingerden

[11] Patent Number: Plant 6,512

[45] Date of Patent: Jan. 3, 1989

[54] CHRYSANTHEMUM NAMED 'HELLO DOLLY'

[75] Inventor: Jerry van Wingerden, Carpinteria, Calif.

[73] Assignee: California Plant Company, Carpinteria, Calif.

[21] Appl. No.: 42,031

[22] Filed: Apr. 24, 1987

[51] Int. Cl.[4] ..... A01H 5/00

[52] U.S. Cl. ..... Plt./76

[58] Field of Search ..... Plt./76

*Primary Examiner*—James R. Feyrer

*Attorney, Agent, or Firm*—Charles W. Rummler

[57] ABSTRACT

A new variety of *Chrysanthemum morifolium,* Ramat, for greenhouse culture having a nine-week response for recurrent year-round profuse production of medium sized, long lasting flowers, this plant being a sturdy and rapid grower with abundant foliage and being particularly suited for greenhouse culture within normal Chrysanthemum growing procedures.

1 Drawing Sheet

BACKGROUND OF THE NEW PLANT

This new variety of Chrysanthemum was discovered by me as a sport of the unpatented variety 'Dolly' being grown in my greenhouse at Carpinteria, Calif., and this particular bloom quickly attracted my attention because of its considerably darker coloration than the parent variety, as well as that of the variety 'Diana' (U.S. Plant Pat. No. 5,496) which is also being grown in my greenhouse. Because of the unusual coloration of this sport, I propagated it by means of cuttings through several successive generations and found that the propagated plants retained all of the physiological characteristics of the parent 'Dolly', except for flower coloration, and that the color characteristics of the new plant hold true from generation to generation and appear to be firmly fixed. This new plant provides a valuable addition to the market for this type of Chrysanthemum as exemplified by the success of 'Dolly' and 'Diana'.

DESCRIPTION OF THE DRAWING

My new variety of Chrysanthemum plant is illustrated by the accompanying full color photographic drawings which, in in the upper view, shows a cluster of blooms of my new variety, and the lower view shows a comparison of the blooms of the new plant with the blooms of 'Diana' and 'Dolly', the flowers of the new plant being at the left side of the picture and the blooms of 'Diana' being in the center of the group, the color characteristics of the flowers being shown as nearly true as is reasonably possible to obtain by means of conventional photographic procedures.

DESCRIPTION OF THE NEW PLANT

The following is a detailed description of my new variety of Chrysanthemum plant with color designations according to The R.H.S. Colour Chart published by The Royal Horticultural Society at London, England.

THE PLANT

Origin: Sport.
Parentage: The unpatented variety 'Dolly'.
Classification:
- *Botanic.*—*Chrysanthemum morifolium,* Ramat.
- *Commercial.*—Greenhouse Chrysanthemum.

Form: Herbaceous bush.
Height: About 120 cm.
Growth: Vigorous, sturdy and semi-upright with good strength.
Growth rate: Rapid.
Response: Nine weeks.
Branching: Normal.
Foliage:
- *Quantity.*—Abundant.
- *Shape.*—Lobed ovate with slightly to moderately serrated margins.
- *Texture.*—Smooth and leathery.
- *Color.*—Upper side — 137A. Under side — 138A.
- *Ribs and veins.*—Prominent.
- *Stipules.*—Rudimentary.

THE BUD

Form: Oval-flattened.
Size:
- *Diameter.*—1 cm.
- *Depth.*—0.7 cm.

Opening rate: Slow.
Color:
- *When sepals first divide.*—157C.
- *When petals begin to unfurl.*—77A.

Sepals:
- *Shape.*—Curved. The sepals are hooded over the bud. When the flowers open, the sepals curl back.
- *Number.*—Approximately ten.
- *Color.*—Inside — 137B. Outside — 137A.

Calyx:
- *Shape.*—Funnel-shaped.

Peduncle:
- *Length.*—Nine inches.

THE FLOWER

Blooming habit: Recurrent and profusely with controlled photoperiod.
Natural blooming period: Fall.
Size: Medium. About three inches and one-half inches in diameter.
Borne: In clusters on elongated pedicels.
Shape: When bloom first opens and as it matures, flat.
Petalage:
- *Number of ray florets.*—About 260.

*Arrangement.*—Composite and whorled on the receptacle.

*Shape.*—Open at the base and quickly broadening to a wide, flat keel which tapers to a blunt point.

*Color.*—Outer Petals: Upper side — 78C and 77C. Reverse side — 75A and 75B.

*Texture.*—Soft.

*Aspect.*—Satiny.

Peduncle: Nine inches long.

Persistence: Resists shattering.

Discoloration after full bloom: The color becomes somewhat lighter.

Fragrance: Typical Chrysanthemum.

REPRODUCTIVE ORGANS

Stamens:

*Number.*—Nine, in average.

*Arrangement.*—Clustered in center of flower.

*Filaments.*—Length: 2.5 mm. Color: 157A.

*Anthers.*—Color: Yellow.

*Pollen.*—Color: Yellow.

Pistils:

*Number.*—One per ray floret.

*Styles.*—Length: 5 mm. Color: Yellow.

*Stigma.*—Color: Yellow.

Characteristics of ovaries: Numerous, and attached to receptacle, and having opaque white color.

This new Chrysanthemum variety most nearly resembles 'Diana', U.S. Plant Pat. No. 5,496, and 'Dolly', which is an unpatented commercial variety. The form of my new Chrysanthemum is similar to that of 'Dolly' but has fewer petals and the color is much darker. The color of the new variety is darker than 'Diana' and also has fewer petals and the petals of my new variety are flatter and less rolled than those of 'Diana' giving it a smoother and less ragged appearance.

The following is a comparison chart illustrating the color distinctions of my new variety 'Hello Dolly' with respect to the parent plant 'Dolly' and the similar plant 'Diana', as observed in my greenhouse at Carpinteria, Calif.

| Flower: | Hello Dolly | Diana | Dolly |
|---|---|---|---|
| Upper Side Color: | 77C–78C | 75A–75B | 75C and D |
| Reverse Side Color: | 75A–75B | 75C | 75D |
| Number of Petals: | 260 | 315 | 308 |

The colors will vary somewhat with changes of season and growing techniques; the new plant, however, is always darker than 'Diana'.

I claim:

1. A new and distinct variety of Chrysanthemum and parts thereof, substantially as herein shown and described, particularly characterized by the darker color of the ray and disc florets of the flower as compared to the color of the parent plant, the physiological characteristics of the new plant being substantially the same as those of the parent.

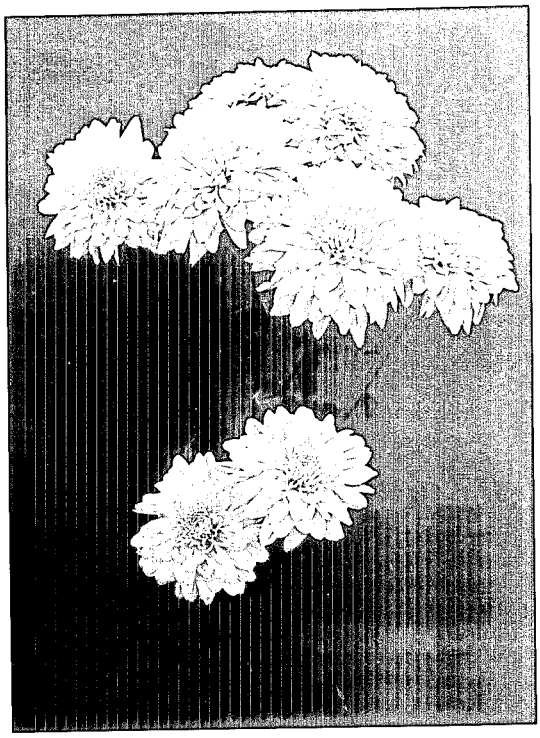
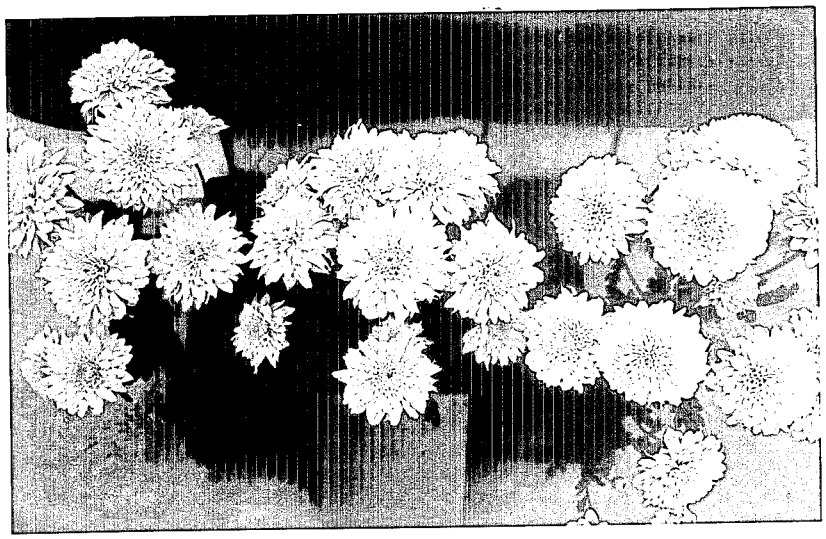

* * * * *